(12) United States Patent
Araoka

(10) Patent No.: US 8,397,170 B2
(45) Date of Patent: Mar. 12, 2013

(54) MEDICAL IMAGE DISPLAY APPARATUS

(75) Inventor: Junichiro Araoka, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 494 days.

(21) Appl. No.: 11/134,360

(22) Filed: May 23, 2005

(65) Prior Publication Data

US 2005/0259116 A1 Nov. 24, 2005

(30) Foreign Application Priority Data

May 24, 2004 (JP) ................ P2004-152723
May 18, 2005 (JP) ................ P2005-144882

(51) Int. Cl.
*G06F 3/048* (2006.01)
(52) U.S. Cl. ........ 715/764; 715/763; 715/778; 715/782; 715/783; 715/789; 715/794; 715/803
(58) Field of Classification Search .................... 715/764
See application file for complete search history.

(56) References Cited

U.S. PATENT DOCUMENTS

| | | | | |
|---|---|---|---|---|
| 6,081,267 A * | 6/2000 | Stockham et al. | ............ | 715/788 |
| 6,333,752 B1 * | 12/2001 | Hasegawa et al. | ............ | 715/764 |
| 6,734,880 B2 * | 5/2004 | Chang et al. | ................. | 715/738 |
| 6,859,219 B1 * | 2/2005 | Sall | ................................ | 345/1.1 |
| 6,976,228 B2 * | 12/2005 | Bernhardson | ................. | 715/830 |
| 7,415,662 B2 * | 8/2008 | Rothmuller et al. | ............ | 715/200 |
| 7,438,685 B2 * | 10/2008 | Burdette et al. | ............... | 600/439 |
| 2002/0047869 A1 * | 4/2002 | Takiguchi | ..................... | 345/838 |
| 2003/0212327 A1 * | 11/2003 | Wang et al. | ................... | 600/437 |
| 2004/0073417 A1 * | 4/2004 | Rubbert et al. | ................ | 703/11 |
| 2004/0201752 A1 * | 10/2004 | Parulski et al. | .......... | 348/231.99 |

* cited by examiner

*Primary Examiner* — Steven Sax
*Assistant Examiner* — Anil Kumar
(74) *Attorney, Agent, or Firm* — Oblon, Spivak, McClelland, Maier & Neustadt, L.L.P.

(57) ABSTRACT

A medical image display apparatus stores examination information of a plurality of examinations and image data resulting from the plurality of examinations, displays a plurality of selectable icons corresponding to the plurality of examinations along one of a vertical direction and a horizontal direction in a screen, displays one or more selectable thumbnail images along the other one of the vertical direction and the horizontal direction, and displays an original image based on the image data. Each of the one or more selectable thumbnail images is displayed in a smaller size than the original image. An input unit is configured to select a first of the plurality of selectable icons and a first of the one or more selectable thumbnail images associated with the selected icon, so that an original image corresponding to the selected thumbnail image is displayed.

29 Claims, 14 Drawing Sheets

MEDICAL IMAGE DISPLAY APPARATUS

CROSS-REFERENCE TO RELATED APPLICATION

This application is based upon and claims the benefit of priority from prior Japanese Patent Application Nos. P2004-152723, filed on May 24, 2004 and P2005-144882, filed on May 18, 2005, the entire contents of which are incorporated herein by reference.

BACKGROUND OF THE INVENTION

1. Field of the Invention

The present invention relates to a medical image display apparatus for and a method of displaying a medical image, particularly, displaying an original image corresponding to one selected from a plurality of images displayed in a smaller size than the original image.

2. Discussion of the Background

A medical image system has been introduced, for example, to store and display medical information. The medical information results from a medical imaging apparatus such as, for example, an X-ray diagnosis apparatus, an X-ray computed tomography apparatus, a magnetic resonance imaging apparatus, a nuclear medicine diagnosis apparatus, an ultrasound diagnosis apparatus, an endoscope apparatus, or the like. The medical information includes image information and may also include its accompanying information. The image information is typically stored with its accompanying information in an image storage apparatus such as an image filing server. The image information and its accompanying information may also be stored in an image display apparatus, for example, temporarily.

When the image information and the accompanying information is stored in those apparatuses, the image information and the accompanying information is often stored hierarchically. The accompanying information may include patient information and examination information. For example, the patient information such as a patient name and a patient identification number may be stored as the first layer. Under the first layer, the examination information such as an examination date may be stored as the second layer. In other words, the examination information may relate to examinations which have been conducted on the patient identified by the patient information. In the third layer, the image information is provided including, for example, image data, size-reduced image data prepared based on the image data before or after the reception of the medical information, an imaging condition, and imaging time. The size-reduced image data may be so-called thumbnail image data.

When an operator such as a doctor desires to observe medical images based on the image data in an image display apparatus, the operator typically operates to display a patient list showing the patient information of a plurality of patients. The operator then operates to select one of the patients from the patient list so that an examination list is displayed based on the examination information of a plurality of examinations with respect to the patient selected from the patient list. The operator operates to select one of the examinations from the examination list so that one or more size-reduced images are displayed based on the medical image data with respect to the examination selected from the examination list.

The operator then usually observes the size-reduced images and selects one of the size-reduced images. In response to the selection, an image corresponding to the selected size-reduced image is displayed in a larger size. If the displayed image is desired one, the operator may observe the displayed image for, for example, the diagnosis. If, however, there is no image (or no size-reduced image) desired by the operator in the selected examination, the operator needs to operate to return to the examination list and display the examination list again. The operator may select a different examination from the examination list and repeat the above operations. The above-described operation work is described, for example, in Japanese Patent Application Publication No. PH07-168845.

Since the above-described operation work requires the operator to return to the examination list which is displayed in a display window different from the size-reduced images, the operator may be required to repeatedly change the display windows one from another unless the desired image is found. The examination list may include only information of an examination date and time. In this case, it is difficult for the operator to find the desired image and may result in forcing the operator to select an examination and observe size-reduced images with respect to nearly every examination. As a result, it may take time for the operator to find and observe the desired image.

Further, imaged parts of the patient and the imaging conditions are typically similar among the examinations. Since the size-reduced images usually have less information than their original images, it is not easy to recognize the difference among them, particularly when they are displayed by changing back and forth the examination list window and the size-reduced image window with respect to a plurality of examinations.

SUMMARY OF THE INVENTION

According to the first aspect of the present invention, there is provided a medical image display apparatus including a storage unit, a display unit, and an input unit. The storage unit is configured to store examination information of a plurality of examinations and image data resulting from the plurality of examinations. The display unit is configured to display a plurality of selectable icons corresponding to the plurality of examinations along one of a vertical direction and a horizontal direction in a screen. The display unit is also configured to display one or more selectable thumbnail images along the other one of the vertical direction and the horizontal direction. The display unit is still further configured to display an original image based on the image data. Each of the one or more selectable thumbnail images is displayed in a smaller size than the original image. The input unit is configured to select a first of the plurality of selectable icons and a first of the one or more selectable thumbnail images. The one or more selectable thumbnail images belong to a first of the plurality of examinations which corresponds to the first selectable icon. The original image corresponds to the first selectable thumbnail image.

According to the second aspect of the present invention, there is provided a medical image display apparatus including a storage unit, a display unit, and an input unit. The storage unit is configured to store examination information of a plurality of examinations and image data resulting from the plurality of examinations. The display unit is configured to display a plurality of icons corresponding to the plurality of examinations along one of a vertical direction and a horizontal direction in a screen. The display unit is further configured to display one or more selectable thumbnail images for each of the plurality of icons along the other one of the vertical direction and the horizontal direction. The display unit is still further configured to display at least one original image based on the image data. Each of the one or more selectable thumbnail images is displayed in a smaller size than each of the at least one original image. The input unit is configured to select at least one of the one or more selectable thumbnail images. The at least one original image corresponds to the selected at least one of the one or more selectable thumbnail images.

According to the third aspect of the present invention, there is provided a medical image display apparatus including a storage unit, a display unit, and an input unit. The storage unit is configured to store imaging information of a plurality of imaging operations and a plurality of image data sets resulting from the plurality of imaging operations, respectively. Each of the image data sets includes a series of images. The display unit is configured to display a plurality of selectable icons corresponding to the plurality of imaging operations along one of a vertical direction and a horizontal direction in a screen. The display unit is further configured to display one or more selectable thumbnail images along the other one of the vertical direction and the horizontal direction. The display unit is still further configured to display at least one of the series of images based on the image data set. Each of the one or more selectable thumbnail images is displayed in a smaller size than each of the at least one of the series of images. The input unit is configured to select one of the plurality of selectable icons and one of the one or more selectable thumbnail images. The one or more selectable thumbnail images belong to a first of the plurality of imaging operations which corresponds to the selected one selectable icon. The at least one of the series of images corresponds to the selected one selectable thumbnail image.

According to the fourth aspect of the present invention, there is provided a method of displaying a medical image. The method begins by storing examination information of a plurality of examinations and image data resulting from the plurality of examinations and displaying a plurality of selectable icons corresponding to the plurality of examinations along one of a vertical direction and a horizontal direction in a screen. The method continues by selecting a first of the plurality of selectable icons and displaying the one or more selectable thumbnail images along the other one of the vertical direction and the horizontal direction. The one or more selectable thumbnail images belong to a first of the plurality of examinations which corresponds to the first selectable icon. The method still continues by selecting a first of the one or more selectable thumbnail images and displaying an original image based on the image data. The original image is displayed in a larger size than the first selectable thumbnail image. The original image corresponds to the first selectable thumbnail image.

According to the fifth aspect of the present invention, there is provided a method of displaying a medical image. The method begins by storing examination information of a plurality of examinations and image data resulting from the plurality of examinations. The method continues by displaying a plurality of icons corresponding to the plurality of examinations along one of a vertical direction and a horizontal direction in a screen and displaying one or more selectable thumbnail images for each of the plurality of icons along the other one of the vertical direction and the horizontal direction. The method still continues by selecting at least one of the one or more selectable thumbnail images and displaying at least one original image based on the image data. The at least one original image is displayed in a larger size than each of the one or more selectable thumbnail images. The at least one original image corresponds to the selected at least one of the one or more selectable thumbnail images.

According to the sixth aspect of the present invention, there is provided a method of displaying a medical image. The method begins by storing examination information of a plurality of examinations and image data resulting from the plurality of examinations displaying a plurality of selectable icons corresponding to the plurality of examinations along one of a vertical direction and a horizontal direction in a screen. The method continues by selecting a first of the plurality of selectable icons and displaying a first set of one or more selectable thumbnail images along the other one of the vertical direction and the horizontal direction. The first set belongs to a first of the plurality of examinations which corresponds to the first selectable icon. The method still continues by selecting a second of the plurality of selectable icons and switching to display the first set to a second set of one or more selectable thumbnail images. The second set belongs to a second of the plurality of examinations which corresponds to the second selectable icon. The method further continues by selecting a first selectable thumbnail image from the second set and displaying an original image corresponding to the first selectable thumbnail image based on the image data. The original image is displayed in a larger size than the first selectable thumbnail image.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings.

A medical image display apparatus according to the embodiments may be used to display medical images resulting from medical imaging apparatuses such as, for example, an X-ray diagnosis apparatus, an X-ray computed tomography apparatus, a magnetic resonance imaging apparatus, a nuclear medicine diagnosis apparatus, an ultrasound diagnosis apparatus, an endoscope apparatus, and/or the like. The feature of the medical image display apparatus to be described below may also be implemented in other apparatuses such as, for example, the medical imaging apparatuses.

First Embodiment

Figure 1:
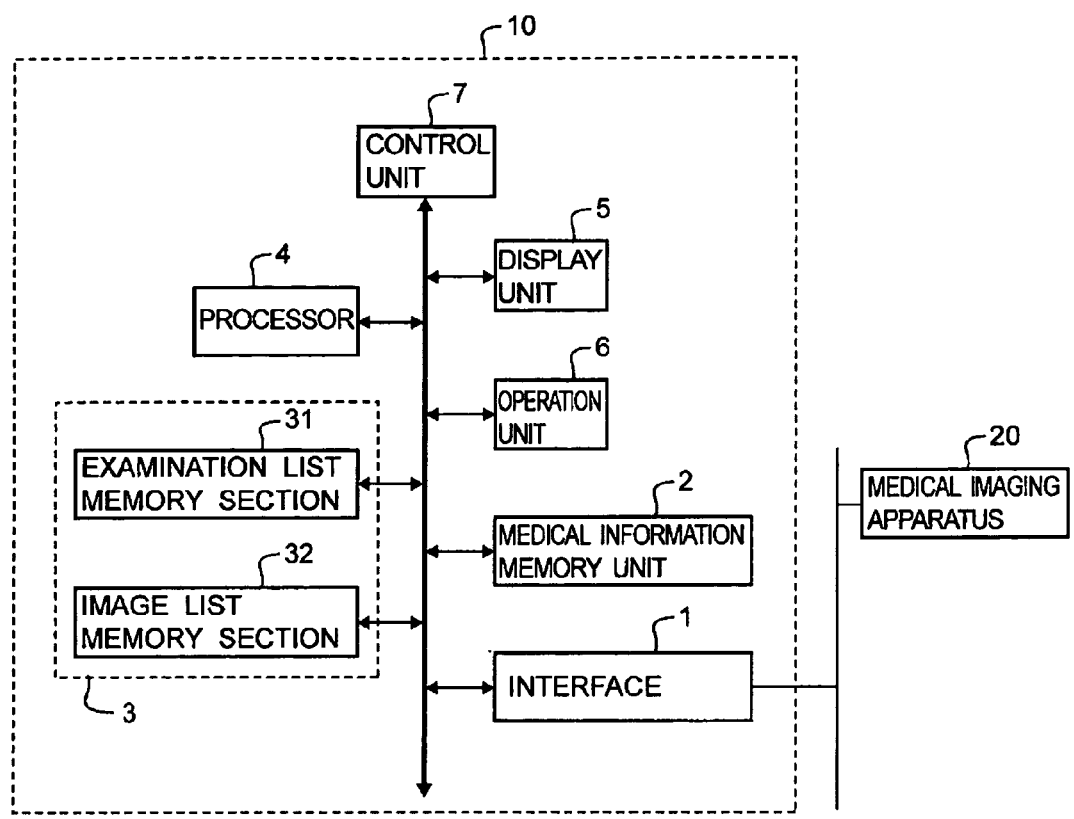
FIG. 1 is a block diagram showing an exemplary configuration of a medical image display apparatus according to the first embodiment.

FIG. 1 is a block diagram showing an exemplary configuration of a medical image display apparatus according to the first embodiment. As shown in FIG. 1, a medical image display apparatus 10 includes an interface 1, a medical information memory unit 2, a buffer memory unit 3, a processor 4, a display unit 5, an operation unit 6, and a control unit 7.

The interface 1 is connected to a medical imaging apparatus 20 through a network and receives medical information including image information and its accompanying information from the medical imaging apparatus 20. The medical imaging apparatus 20 may be one or more of the abovementioned medical imaging apparatuses. The image information may include image data and imaging condition information including imaging time information. The image data may be two-dimensional image data, three-dimensional image data, motion image data, and/or the like, which result in one or more two-dimensional images, one or more three-dimensional images, one or more motion images, and/or the like. Each motion image includes a series of images (a plurality of images), that is, for example, a series of frame images or slice images. When the interface 1 is operative as a disk drive, the interface 1 may receive the medical information stored in a memory medium such as a CD-R, DVD, or the like. The received medical information may be provided to the medical information memory unit 2.

The medical information memory unit 2 stores the medical information received by the interface 1. The medical information memory unit 2 may include a memory device such as, for example, a magnetic disk. The buffer memory unit 3 includes an examination list memory section 31 and an image list memory section 32. The examination list memory section 31 stores the examination information with respect to specific patient information included in the accompanying information. The examination information may be extracted from the medical information (or the accompanying information) stored in the medical information memory unit 2. The image list memory section 32 stores the image information with respect to the specific patient information. The image information may be extracted from the medical information stored in the medical information memory unit 2.

The processor 4 prepares reference image data to be displayed as reference images in a smaller size than original images based on the image data included in the medical information. The reference images may be, for example, thumbnail images, size-reduced images, or the like and are hereinafter referred to as thumbnail images. The reference image data are also hereinafter referred to as thumbnail image data. The thumbnail image data are stored as part of the image information in the medical information memory unit 2. The thumbnail image data with respect to the specific patient information are also stored in the image list memory section 32. The processor 4 also prepares icon data with respect to the examination information. Details of the icon data will be described later. The prepared icon data are stored as part of the examination information in the medical information memory unit 2. The icon data with respect to the specific examination information are also stored in the examination list memory section 31.

The processor 4 extracts the icon data stored in the examination list memory section 31 and the thumbnail image data stored in the image list memory station 32. The extracted icon data and thumbnail image data are transferred to the display unit 5. The display unit 5 may include a cathode ray tube (CRT) display or a liquid crystal display (LCD) and display the patient information, the examination information, and the image information stored in the medical information memory unit 2. The display unit 5 also displays icons based on the icon data transferred from the processor 4 and thumbnail images based on the thumbnail image data transferred from the processor 4.

The operation unit 6 may include one or more input devices such as, for example, a keyboard, a trackball, a mouse, and a joystick. The operation unit 6 may also include a touch panel and/or various switches (buttons). The operation unit 6 is used to input information for designation, instruction, and selection and may be operative as an interactive interface.

The control unit 7 includes a central processing unit (CPU) and memory circuitry and controls over the medical image display apparatus 10. Particularly, the control unit 7 receives the information input from the operation unit 6, temporarily stores the input information in the memory circuitry, and controls the interface 1, the medical information memory unit 2, the buffer memory unit 3, the processor 4, and the display unit 5 based on the input information.

Figure 2:
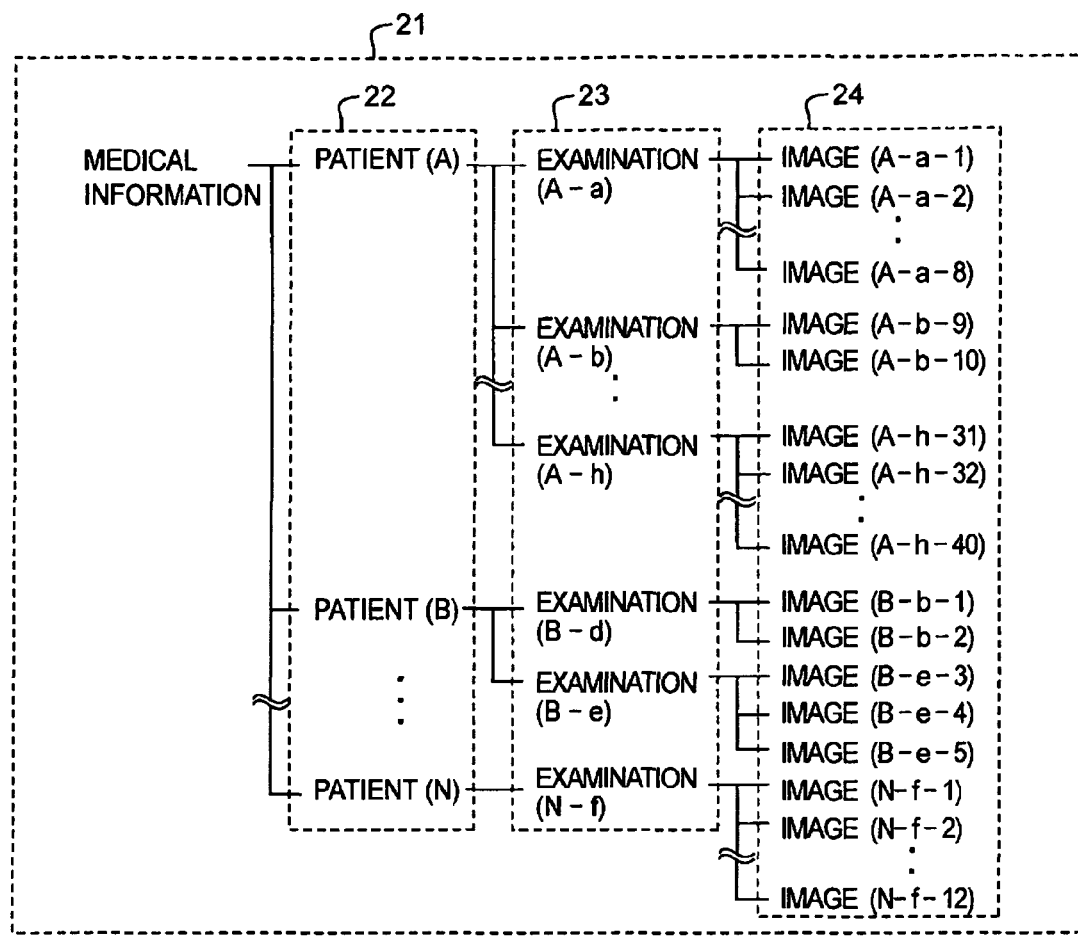
FIG. 2 is an illustration showing an exemplary form of storing medical information in a medical information memory unit.

FIG. 2 is an illustration showing an exemplary form of storing the medical information in the medical information memory unit 2. As shown in FIG. 2, the medical information is stored in a database 21 of the medical information memory unit 2 in a form of three layers. In the first layer 22, patient information (A) to (N) is stored. For example, the patient information (A), (B), to (N) pertains to patients A, B, to N, respectively. Taking the patient information (A) as an example, the patient information (A) includes, for example, a patient name and patient identification information, a sex, a date of birth, and any other necessary information of the patient A. Under the patient information (A), examination information of the patient A is stored as the second layer 23. Examination information (A-a) to (A-h) is listed as the examination information of the patient A. This means that examinations A-a to A-h have been conducted on the patient A. Similarly, examination information (B-d) and (B-e) is listed under the patient information (B). Also examination information (N-f) is listed under the patient information (N). Taking the examination information (A-a) as an example, the examination information (A-a) includes, for example, a date of examination, information of an imaged part of the patient A, a type of imaging (or a type of a medical imaging apparatus) icon data, and any other necessary information with respect to the examination A-a.

The examination information (A-a) to (A-h) may be stored in a time-series order from the earliest (A-a) to the latest (A-h).

Figure 3A:
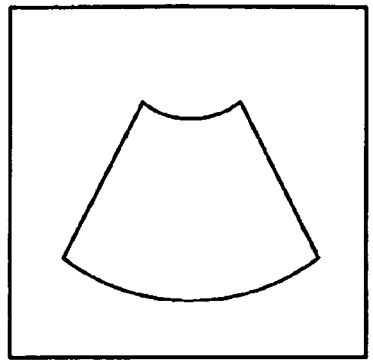
FIGS. 3A to 3C are illustrations showing examples of an icon.
Figure 3B:
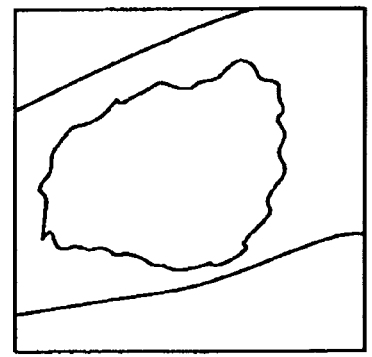
Figure 3C:
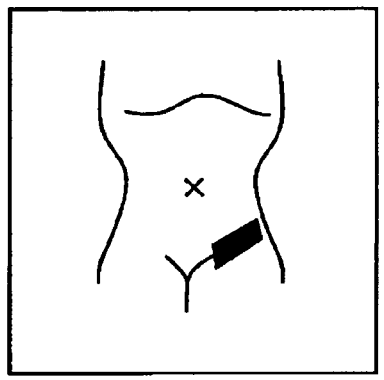

One icon to be displayed based on the icon data represents one examination when the icon is displayed in the display unit 5. Therefore, each of the examination information (A-a) to (A-h) includes icon data. The icon data can be prepared in various ways. For example, when the image data pertains to a motion image or to a plurality of images resulting from the examination A-a, the icon data may be prepared to show an icon showing one image included in the motion image or one of the plurality of images as shown in FIG. 3A. That is, the icon shows a size-reduced image of the one image. The one image may be, for example, the first image, a last image, a marked image, or an image most featuring the motion image or the plurality of images. The icon data may alternatively be prepared to show an icon showing a photograph of a bruise or a wound of the patient A as shown in FIG. 3B or a photograph showing other part of the patient A. These icons may relate to a specific condition of the patient A. The icon data may also be prepared in common among the patients A to N. For example, an icon based on the icon data may show a medical imaging apparatus used in an examination or an imaged (or examined) part of a patient as shown in FIG. 3C.

In FIG. 2, under the examination information (A-a), image information resulting from the examination A-a is stored as the third layer 24. Image information (A-a-1) to (A-a-8) is listed as the image information resulting from the examination A-a. Similarly, image information (A-b-9) and (A-b-10) is listed as the image information resulting from the examination A-b. Other image information with respect to the examinations A-h, B-d, B-e, and N-f is listed as shown in FIG. 2.

Taking the image information (A-a-1) as an example, the image information (A-a-1) includes, for example, image identification information, imaging condition information including imaging time information, image data, thumbnail image data, electrocardiography information, and any other necessary information with respect to an image A-a-1.

The image information (A-a-1) to (A-a-8) may be stored in a time-series order from the earliest (A-a-1) to the latest (A-a-8).

Figure 4:
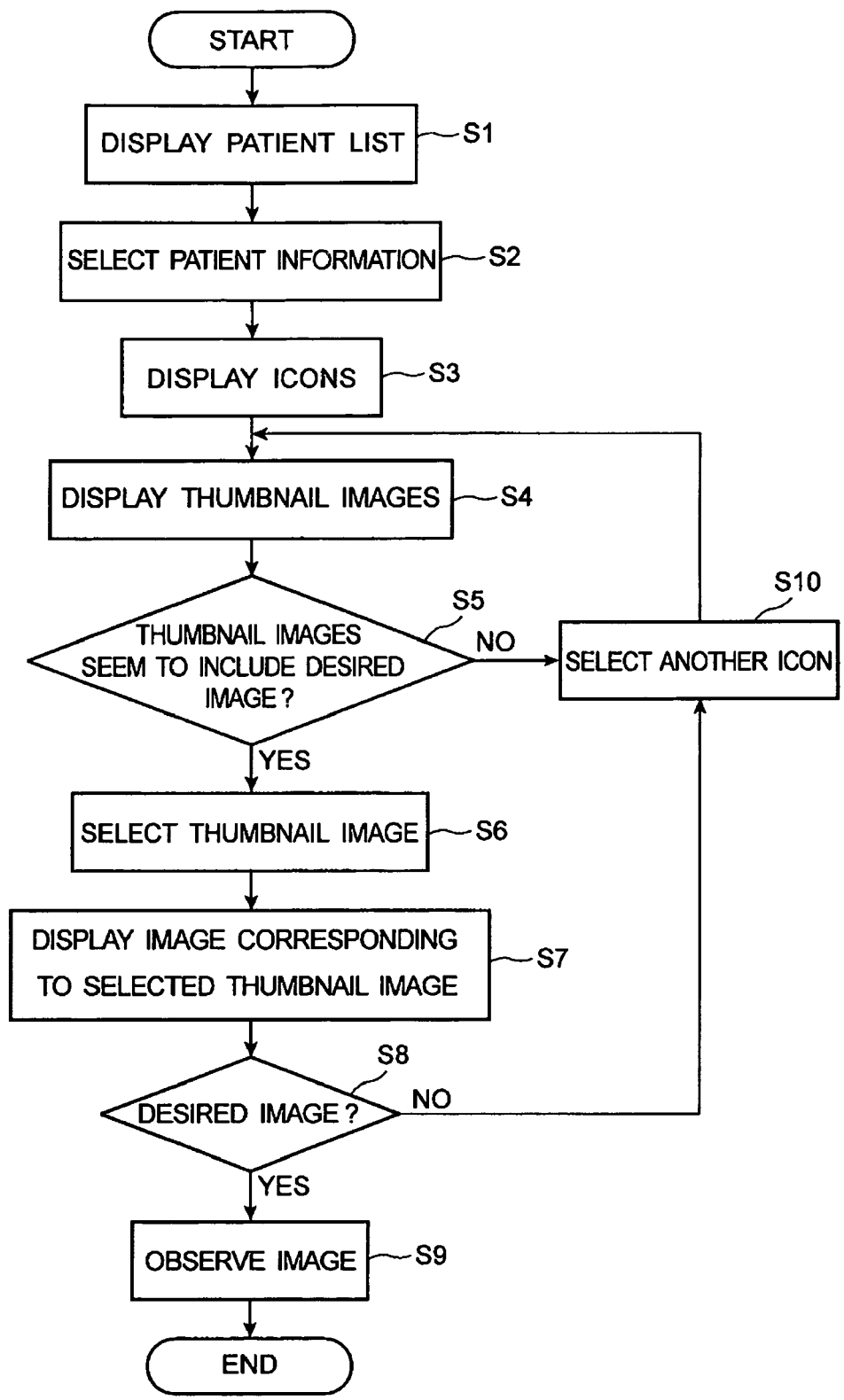
FIG. 4 is a flowchart showing an example of a flow of displaying a desired image according to the first embodiment.

FIG. 4 is a flowchart showing an example of a flow of displaying a desired image according to the first embodiment. An operator of the medical image display apparatus 10 such as, for example, a doctor operates the operation unit 6 so that the patient list stored in the first layer 22 in the medical information memory unit 2 is displayed in the display unit 5 (step S1). The displayed patient list may include the patient information (A) to (N). When the operator needs to observe a specific image with respect to the patient A, the operator selects the patient information (A), using the operation unit 6 (step S2).

In response to the selection of the patient information (A), the examination information (A-a) to (A-h) stored in the second layer 23 in the medical information memory unit 2 is transferred to and temporarily stored in the examination list memory section 31. Also the image information with respect to the examinations A-a to A-h of the patient A such as the image information (A-a-1) to (A-h-40) stored in the third layer 24 in the medical information memory unit 2 is transferred to and temporarily stored in the image list memory section 32. The processor 4 extracts icon data included in the examination information (A-a) to (A-h) stored in the examination list memory section 31. The extracted icon data are transferred to the display unit 5. The display unit 5 displays icons as an examination list of the patient A based on the extracted icon data (step S3). The processor 4 also extracts thumbnail image data included, for example, in the image information (A-a-1) to (A-a-8) stored in the image list memory section 32. The extracted thumbnail image data are transferred to the display unit 5. The display unit 5 may display thumbnail images as an initial image list of the patient A based on the extracted thumbnail image data (step S4).

Figure 5:
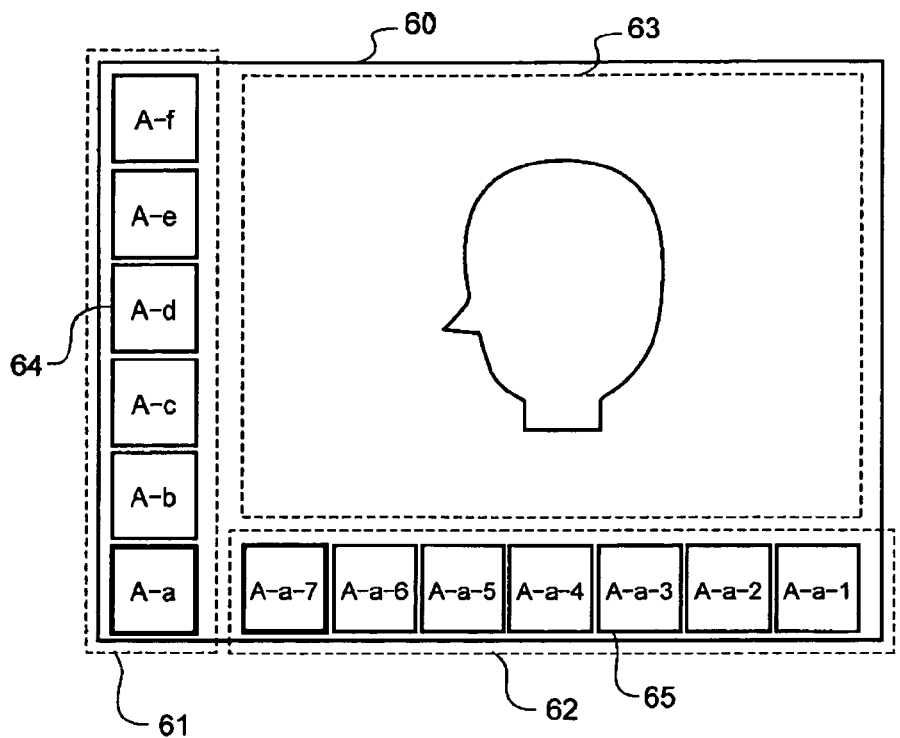
FIG. 5 is an illustration showing the first example of an image display in a display unit according to the first embodiment.

FIG. 5 is an illustration showing an example of an image display in the display unit 5 according to the first embodiment. As shown in FIG. 5, when the display unit 5 displays icons 64 and thumbnail images 65, the icons 64 are displayed along a vertical direction in a screen 60. The icons 64 may be displayed in an examination list display field 61 provided on the left side of the screen 60. When the examination list display field 61 is limited in space, the limited number of the icons 64 may be displayed in parallel. In FIG. 5, icons A-a to A-f corresponding to the examinations A-a to A-f are displayed in the examination list display field 61. Icons corresponding to the examinations A-g and A-h may be displayed by scrolling operation in the operation unit 6. After the scrolling operation, the icons A-a and A-b may disappear from the examination list display field 61 while the icons corresponding to the examinations A-g and A-h are displayed. The icons 64 are selectable, using the operation unit 6. The thumbnail images 65 are displayed along a horizontal direction in the screen 60. The thumbnail images 65 may be displayed in an image list display field 62 provided at the bottom of the screen 60. When the image list display field 62 is limited in space, the limited number of the thumbnail images 65 may be displayed in parallel. In FIG. 5, thumbnail images A-a-1 to A-a-7 are displayed in the image list display field 62. A thumbnail image corresponding to the image information A-a-8 (hereinafter referred to as a thumbnail image A-a-8) may be displayed by scrolling operation in the operation unit 6. After the scrolling operation, the thumbnail image A-a-1 may disappear from the image list display field 62 while the thumbnail image A-a-8 is displayed. The thumbnail images 65 are selectable, using the operation unit 6.

Since the thumbnail images A-a-1 to A-a-8 have been determined as the initial thumbnail images to be displayed in the image list display field 62, the icon A-a is highlighted or displayed in a distinguishable manner from other icons. If the initial thumbnail images have not been determined in advance, none of the icons 64 in the examination list display field 61 is highlighted only when the operator selects the icon A-a, using the operation unit 6, the icon A-a may be highlighted. Also, when the initial thumbnail images have not been determined in advance, no thumbnail image may initially be displayed in the image list display field 62. Only when the operator selects the icon A-a, using with the operation unit 6, the icons A-a-1 to A-a-7 may be displayed in the image list display field 62.

When the examination list display field 61 is limited in space, the icons 64 may be given priorities and displayed in accordance with the priorities or in a priority order. One example of priority conditions is an examination date (and time). In this example, an icon corresponding to the latest examination may be given a top priority and placed, for example, at the bottom of the examination list display field 61 while an icon corresponding to the earliest examination may be given the lowest priority and placed, for example, at the top of the examination list display field 61 or scrolled down to be displayed in the end. Therefore, the icon corresponding to the examination A-h may be displayed at the bottom of the examination list display field 61. The icon A-a may not initially be displayed in the examination list display field 61 and only displayed when scrolled down. Another example of the priority conditions is the number of selection times. An icon which has been most often selected in the past or in the last predetermined period may be given a top priority. Alternatively, the number of image reference times may be used as a priority condition. A top priority may be given to an icon corresponding to the examination including original images which have been most often referred to through their icons in the past or in the last predetermined period. Still alternatively, the icons 64 may be displayed in an order as these icons 64 were displayed in the examination list display field 61 in the last use of the medical image display apparatus 10 (i.e., just before terminating the display).

Giving the priorities may be advantageous since the operator can recognize an icon 64 most often used or likely to be used at a predetermined top priority position. In addition, even when all the icons 64 cannot be displayed in parallel in the examination list display field 61, the operator can find icons 64 given high priorities without the scrolling operation.

Similar display techniques may also be applied to the display of the thumbnail images 65 in the image list display field 62. When the image list display field 62 is limited in space, the thumbnail images 65 may be given priorities and displayed in accordance with the priorities or in a priority order. One example of priority conditions is an imaging date (and time). In this example, a thumbnail image corresponding to the latest image in a series of or a plurality of images may be given a top priority and placed, for example, on the left side of the image list display field 62 while a thumbnail image corresponding to the earliest image in the series of or a plurality of images may be given the lowest priority and placed, for example, on the right side of the image list display field 62 or scrolled to be displayed in the end. Therefore, the thumbnail image A-a-8 may be displayed on the left side of the image list display field 62. The thumbnail image A-a-1 may not initially be displayed in the image list display field 62 and only be displayed when scrolled towards the left. Since a series of images are typically displayed in an imaged order, that is, in an order from the earliest to the latest, the above priority results in a reverse order display, compared to the typical display.

Another example of the priority conditions is the number of image reference times. A top priority may be given to a thumbnail image corresponding to the original image which has been most often referred to in the past or in the last predetermined period. Still alternatively, the thumbnail images 65 may be displayed in an order as these thumbnail images 65 were displayed in the image list display field 62 in the last use of the medical image display apparatus 10 (i.e., just before terminating the display).

Returning to FIG. 4, the operator observes the thumbnail images 65 displayed in the image list display field 62 and determines whether or not the currently displayed thumbnail images includes a thumbnail image corresponding to the specific image which the operator desires to observe (step S5). Since the thumbnail images are displayed in a smaller size than their original images and may lack of some information if the thumbnail image data are prepared by thinning the image data, it may be difficult for the operator to make sure that one thumbnail image definitely corresponds to the desired image. Therefore, in practice, the operator may determine whether the currently displayed thumbnail images seem to include a thumbnail image corresponding to the desired image in step S5.

When the operator determines that there is a thumbnail image corresponding to the desired image in the image list display field 62, the operator operates the operation unit 6 to select the thumbnail image (step S6). FIG. 5 shows a case that the selected thumbnail image is the thumbnail image A-a-7 which is highlighted or displayed in a distinguishable manner from other thumbnail images A-a-1 to A-a-6. In response to the selection of the thumbnail image A-a-7, an original image corresponding to the thumbnail image A-a-7 is displayed in an image display field 63 of the screen 60 (step S7). The original image displayed in the image display field 63 may be enlarged up to and displayed in a full size of the screen 60 by further operation through the operation unit 6. During the enlarged display, the icons 64 and the thumbnail images 65 may disappear from the screen 60. By the way, the original image is an image distinguished from the thumbnail image and does not always have to be an image reproduced from loss less compression image data or based on uncompressed image data.

The operator observes the original image displayed in the image display field 63 and determines whether it is really the desired image or not (step S8). If it is the desired image, the operator continues to observe the original image displayed in the image display field 63 (step S9). The operator may interpret or diagnose the original image according to the necessity.

In step S5, when the operator has not determined that the currently displayed thumbnail images seem to include a thumbnail image corresponding to the desired image, the operator operates the operation unit 6 to select another icon from among the icons A-b to A-f and icons corresponding to the examination A-g and A-h so as to change the thumbnail images 65 displayed in the image list display field 62 (step S10). Accordingly, thumbnail images corresponding to a newly selected icon are displayed in the image list display field 62 in step S4. Also, in step S8, when the operator has not determined that the displayed original image is the desired image, the operator operates the operation unit 6 in the same manner as described above (step S10) although the operator may select another one or more thumbnail images and see if it is the desired image before selecting another icon. Accordingly, thumbnail images corresponding to a newly selected icon are displayed in the image list display field 62 in step S4.

According to the first embodiment described above, the icons 64 representing the examination information, the thumbnail images 65 with respect to one selected from the icons 64, and the original image corresponding to one selected from the thumbnail images 65 are displayed in parallel in the display unit 5. Therefore, the operator is not required to change the display screens (or windows) back and forth in order to select examination information one after another, display thumbnail images, and see if there is a desired image. Accordingly, the operator may be able to obtain the desired image without changing the display screen (or window), which may reduce load of the operator and image observation time. This may lead to improving image observation (or diagnosis) efficiency.

The first embodiment may be modified in the following ways.

Figure 6:
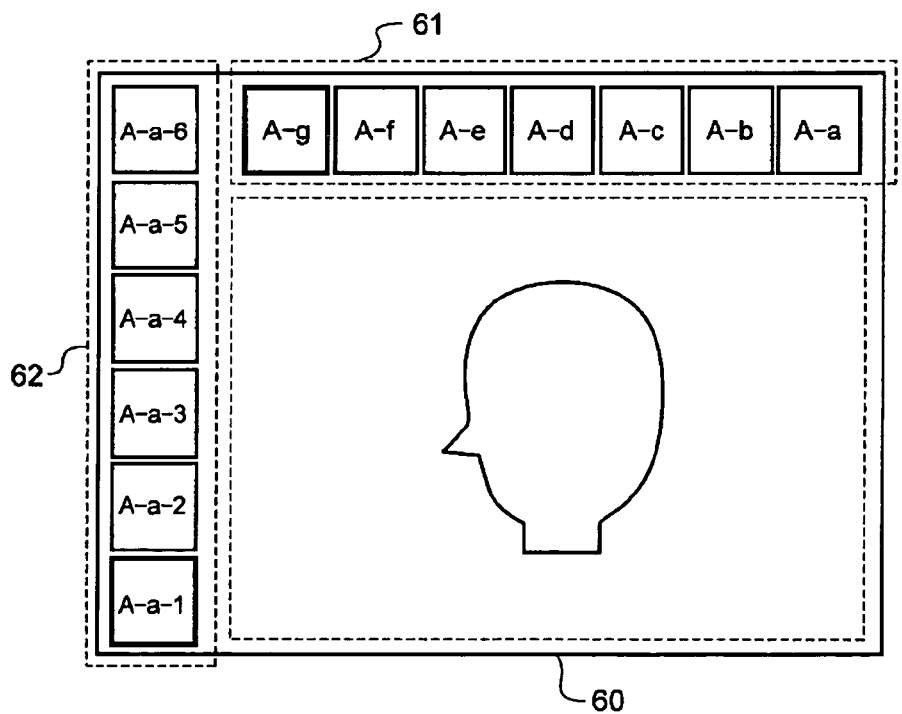
FIG. 6 is an illustration showing the second example of the image display in the display unit according to the first embodiment.

The examination list display field 61 may be provided along the horizontal direction in the screen 60 while the image list display field 62 may be provided along the vertical direction in the screen 60 as shown in FIG. 6.

Figure 7:
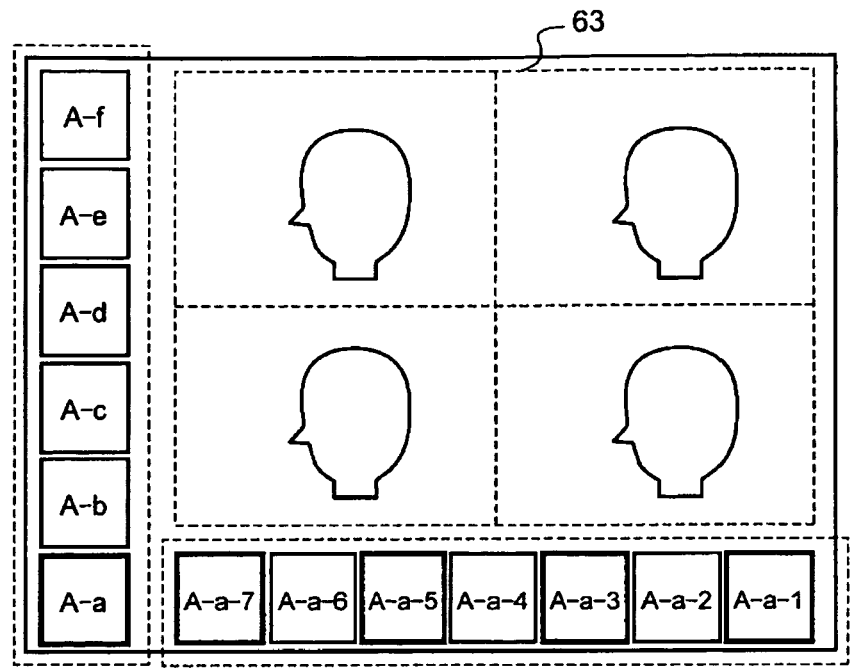
FIG. 7 is an illustration showing the third example of the image display in the display unit according to the first embodiment.

As shown in FIG. 7, the image display field 63 may be divided into a plurality of windows (or a plurality of sections).

Although FIG. 7 shows four sections, any number of sections may be applicable. When a plurality of images are allowed to be displayed in the sections, the operator may select a plurality of thumbnail images (e.g., thumbnail images A-a-7, A-a-5, A-a-3, and A-a-1) so that a plurality of original images corresponding to the selected thumbnail images can be displayed in parallel. Also, the operator may select one or more thumbnail images with respect to one of the icons and one or more thumbnail images with respect to another one of the icons so that original images corresponding to these thumbnail images can be displayed in parallel. Such display may make it possible for the operator to easily compare the original images resulting from different examinations and more effectively or efficiently conduct image observation.

Figure 8:
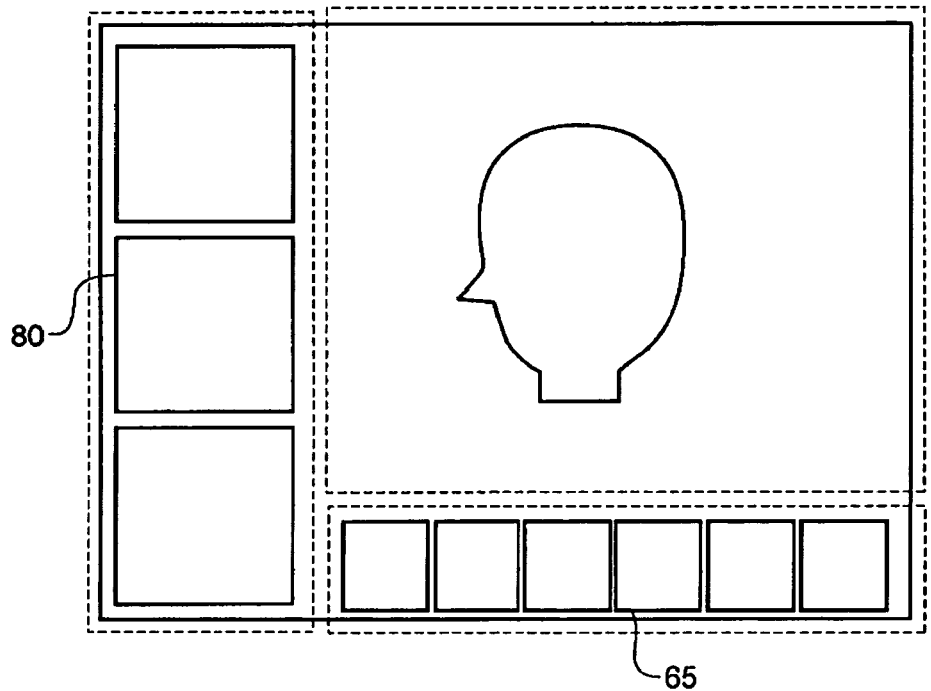
FIG. 8 is an illustration showing the fourth example of the image display in the display unit according to the first embodiment.

As shown in FIG. 8, an icon 80 may be displayed in a larger size than the thumbnail image 65. This may make it easier for the operator to recognize what the icon 80 shows. In addition, the thumbnail images 65 may be displayed in two rows particularly when one icon 80 is displayed in a size twice as high as the thumbnail image 65. Whether the icon 80 is displayed in the larger size or not, the thumbnail images 65 may be displayed in a plurality of rows. Also, the icons may be displayed in a plurality of rows.

Second Embodiment

Figure 9:
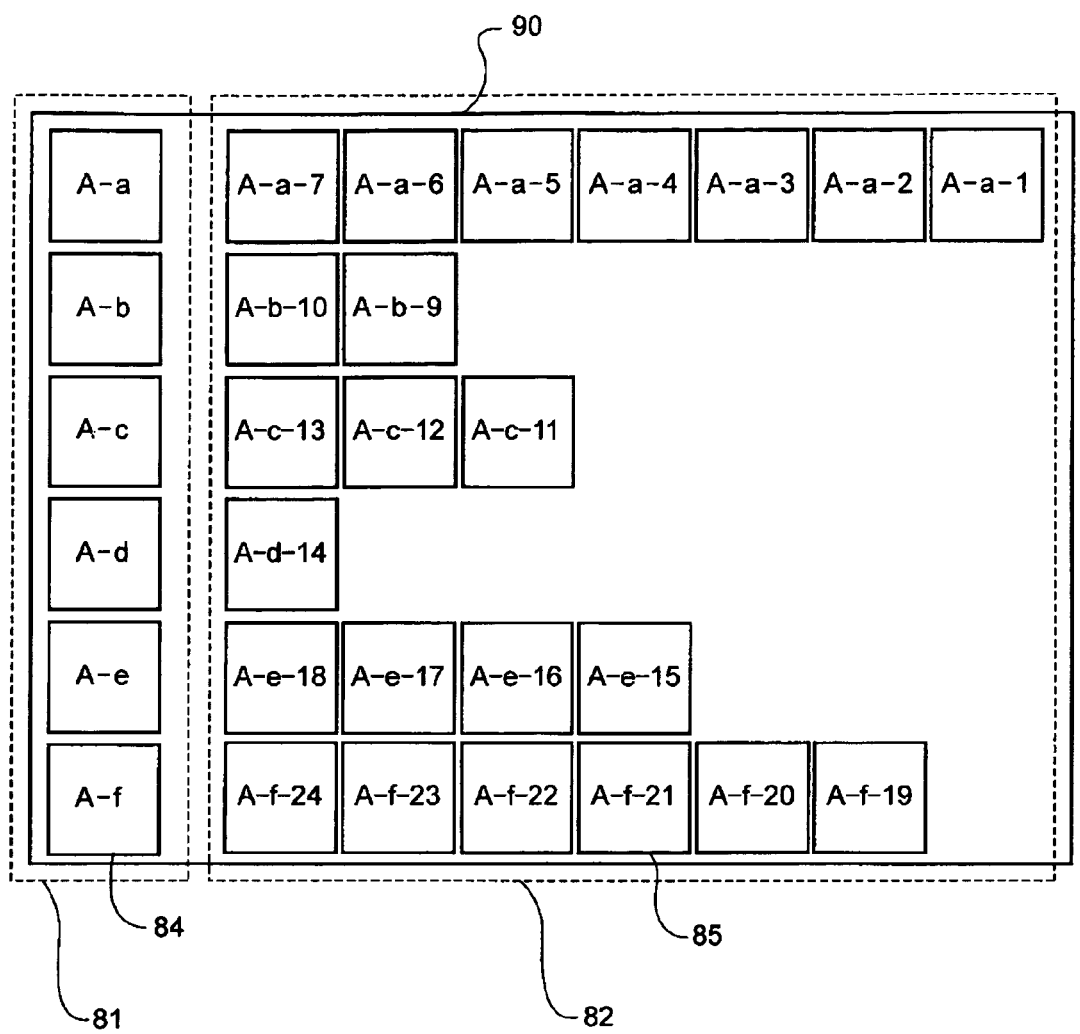
FIG. 9 is an illustration showing the first example of the image display in the display unit according to the second embodiment.

The configuration of the medical image display apparatus 10 shown in FIG. 1 may also be applied to the second embodiment. FIG. 9 is an illustration showing the first example of the image display in the display unit 5 according to the second embodiment.

As similar to FIG. 5, when the display unit 5 displays icons 84 and thumbnail images 85, the icons 84 are displayed along a vertical direction in a screen 90. The icons 84 may be displayed in an examination list display field 81 provided on the left side of the screen 90. When the examination list display field 81 is limited in space, the limited number of the icons 84 may be displayed in parallel. In FIG. 9, icons A-a to A-f corresponding to the examinations A-a to A-f are displayed in the examination list display field 81. Icons corresponding to the examinations A-g and A-h may be displayed by scrolling operation, using the operation unit 6. After the scrolling operation, the icons A-a and A-b may disappear from the examination list display field 81 while the icons corresponding to the examinations A-g and A-h are displayed. The thumbnail images 85 for each of the icons 84 displayed in the examination list display field 81 may be displayed in an image list display field 82 along a horizontal direction in the screen 90 in a manner corresponding to the icons 84. When the image list display field 82 is limited in space for the thumbnail images 85 with respect to one or more specific icons 84, the limited number of the thumbnail images 85 may be displayed in parallel for the specific icons 84. In FIG. 9, thumbnail images A-a-1 to A-a-7 for an icon A-a are displayed in the image list display field 82, but a thumbnail image A-a-8 cannot be displayed with the thumbnail images A-a-1 to A-a-7. The thumbnail image A-a-8 may be displayed by scrolling operation, using the operation unit 6 while the thumbnail image A-a-1 may disappear from the image list display field 82. The thumbnail images 85 are selectable, using the operation unit 6. The scrolling operation may be conducted on the thumbnail images 85 with respect to a selected specific icon 84 such as, for example, the icon A-a as described above. Alternatively, the scrolling operation may be conducted on the thumbnail images 85 with respect to all the icons 84 displayed in the examination list display field 81 all at once.

As similar to the first embodiment, when the operator determines that there is a thumbnail image corresponding to the desired image in the image list display field 82, the operator operates the operation unit 6 to select the thumbnail image 85. The operator may select more than one thumbnail image 85. In this case, the operator may select two or more thumbnail images 85 with respect to specific one of the icons 84. Alternatively, the operator may select thumbnail images 85 with respect to two or more icons 84. In response to the selection of the thumbnail image(s) 85, original image(s) corresponding to the selected thumbnail image(s) 85 may be displayed in a full size of the screen 90. During the display of the original image(s), the icons 84 and the thumbnail images 85 may disappear from the screen 90.

Figure 10:
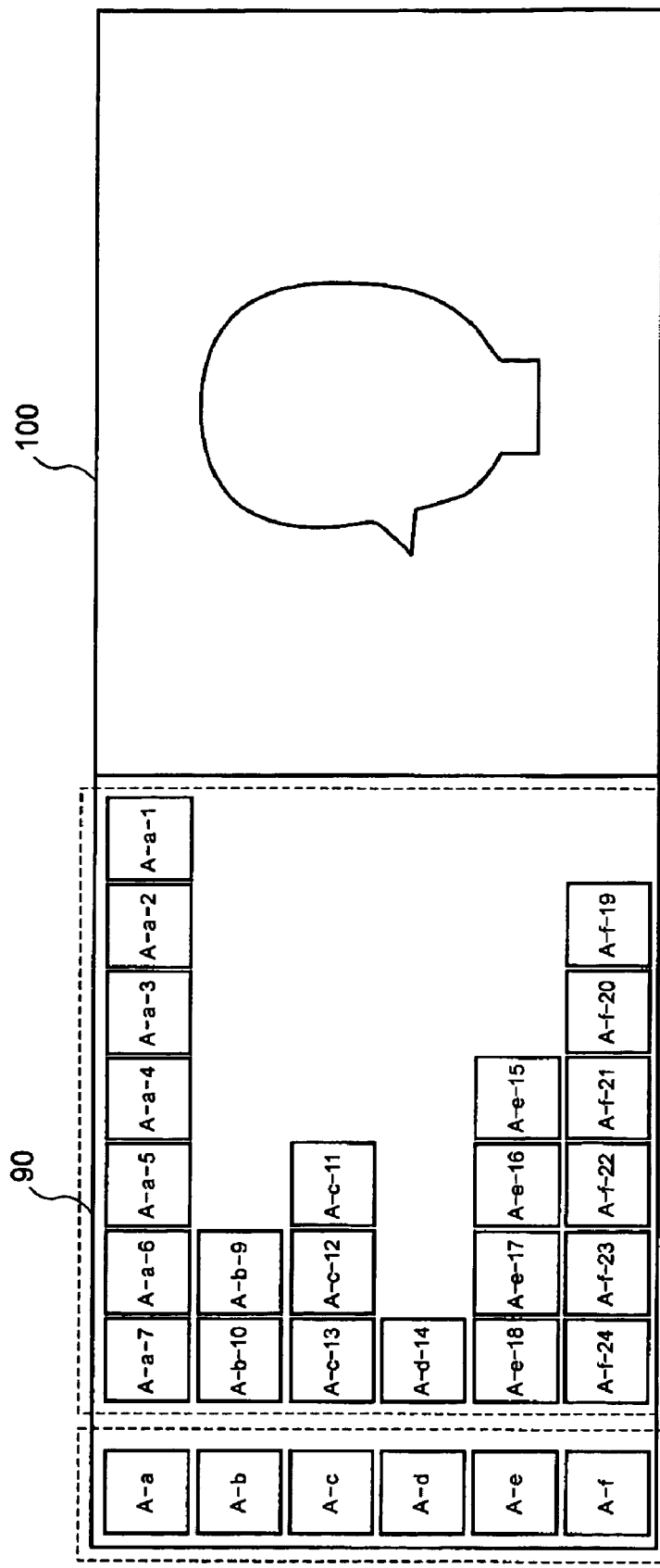
FIG. 10 is an illustration showing the second example of the image display in the display unit according to the second embodiment.

When the display unit 5 includes, for example, two display screens, the original image(s) may be displayed in one of the display screens (a display screen 100) while the icons 84 and the thumbnail images 85 are displayed in the other display screen 90 as shown in FIG. 10.

Figure 11:
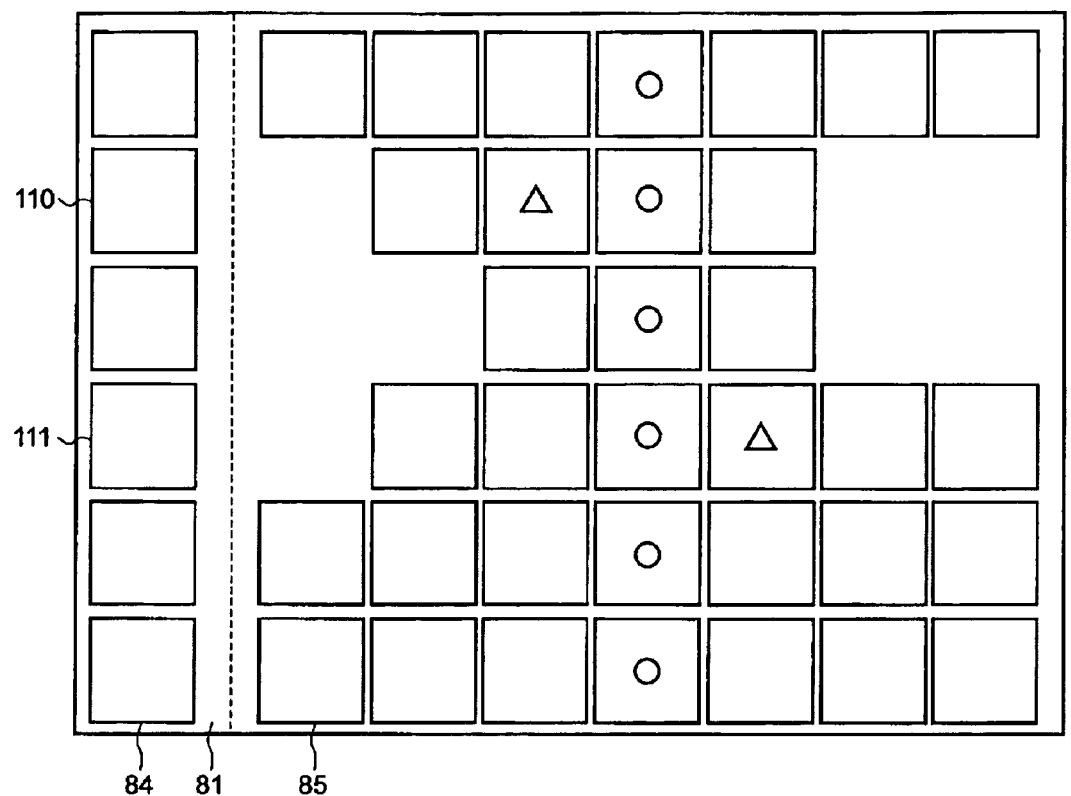
FIG. 11 is an illustration showing an example of the first modification to a display of thumbnail images according to the second embodiment.

The first modification to the display of the thumbnail images 85 is shown in FIG. 11. This modification may be applied when the thumbnail images 85 are based on image data resulting from a magnetic resonance imaging apparatus. As shown in FIG. 11, every central thumbnail image with respect to the icons 84 displayed in the examination list display field 81 is aligned among the icons 84. The thumbnail images 85 marked with a circle are the central thumbnail images.

Figure 12:
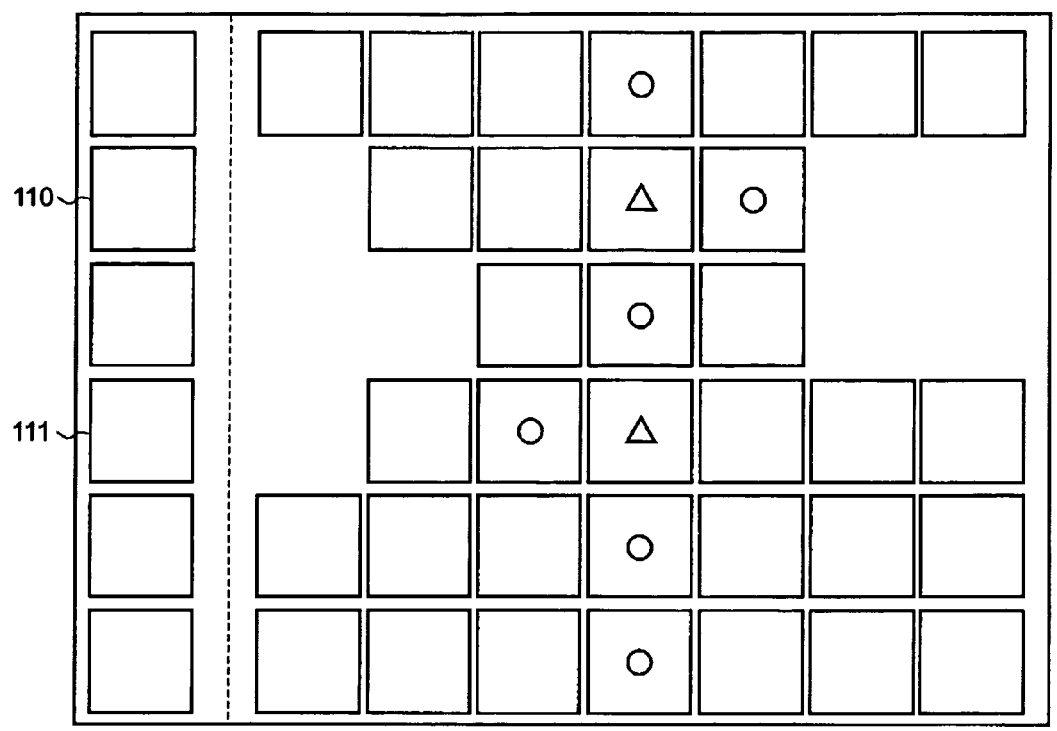
FIG. 12 is an illustration showing an example of a further modification to the first modification.

When the number of the thumbnail images 85 with respect to one icon 84 is even, one of two central thumbnail images may automatically be chosen as an initial central thumbnail image at random or in accordance with a predetermined rule. The operator may, however, not prefer to the one chosen and displayed as the initial central thumbnail image. In this case, the operator may designate the other one of the two central thumbnail images, using the operation unit 6. For example, the operator may designate thumbnail images marked with a triangle as central thumbnail images with respect to specific icons 110 and 111. In response to designation of each or both of the thumbnail images 85 marked with a triangle using the operation unit 6, an instruction input using the operation unit 6 after the designation, or an elapse of a predetermined time after the designation, the thumbnail images 85 marked with a triangle are displayed in alignment with other central thumbnail images 85 marked with a circle as shown in FIG. 12. This may be helpful for the operator to select thumbnail image(s) corresponding to desired image(s).

Figure 13:
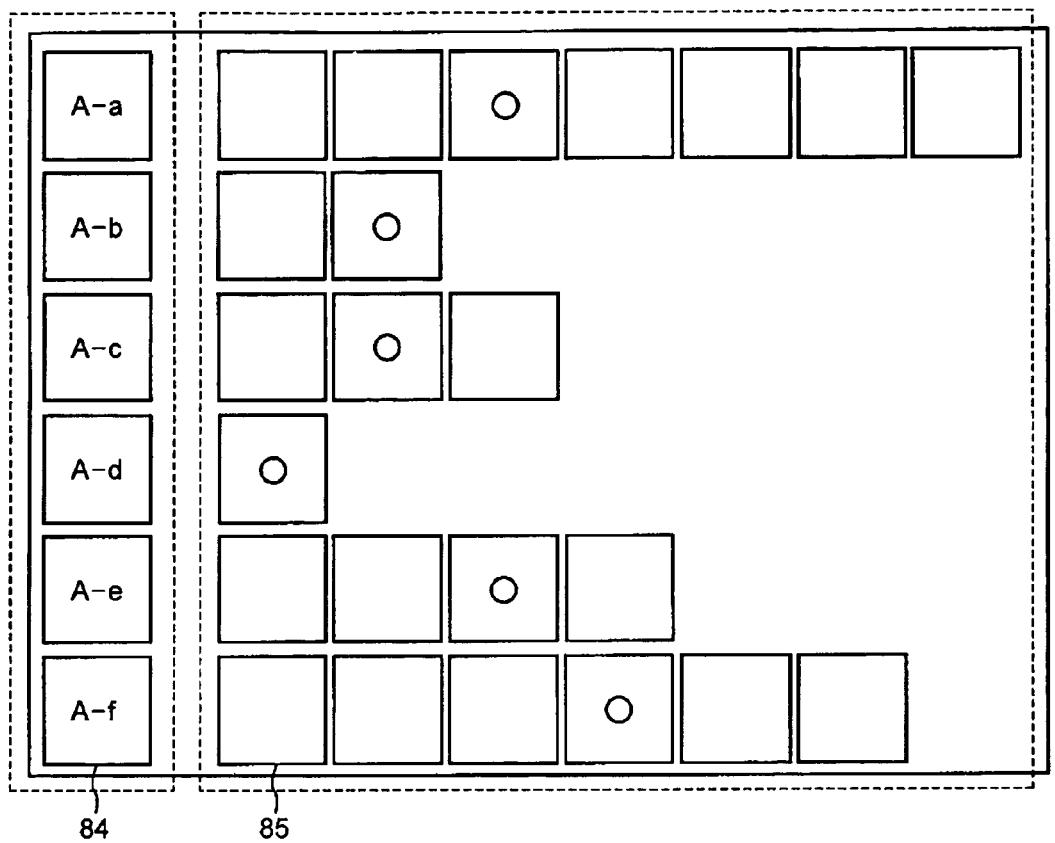
FIG. 13 is an illustration showing an example of thumbnail image selection for the second modification to the image display of thumbnail images according to the second embodiment.
Figure 14:
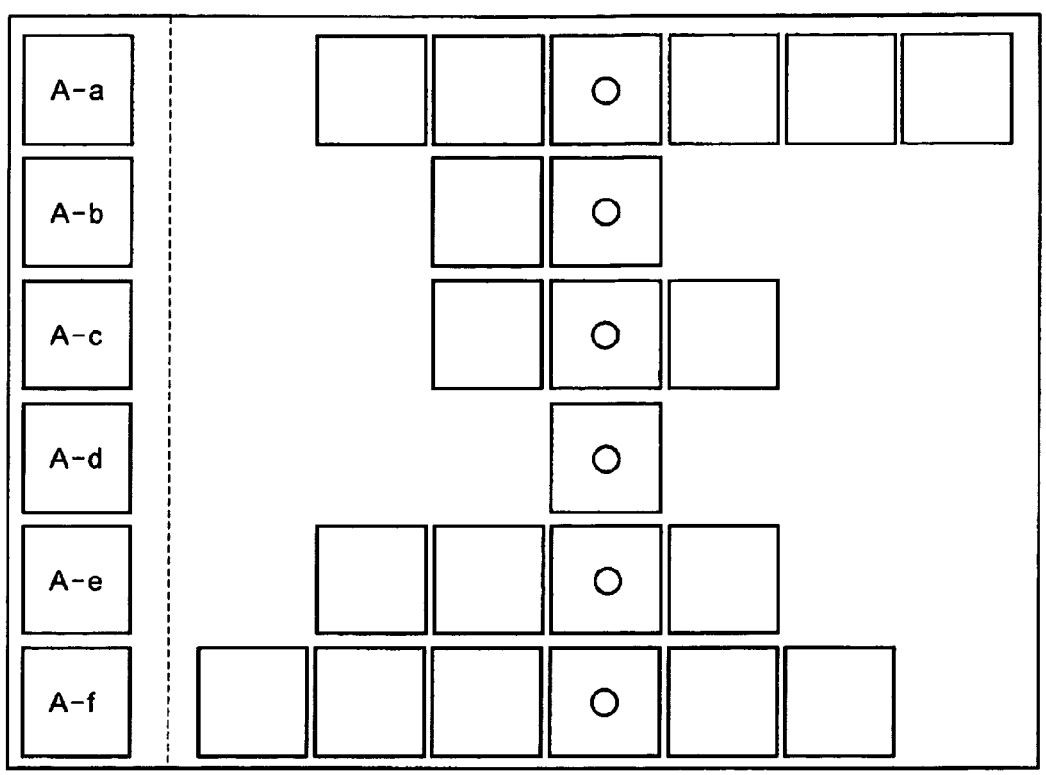
FIG. 14 is an illustration showing an example of the second modification to the display of thumbnail images according to the second embodiment.

The second modification to the display of the thumbnail images 85 will be described with reference to FIGS. 13 and 14. This modification may be applied to the thumbnail images 85 based on image data resulting from any medical imaging apparatus. The thumbnail images 85 are displayed in a manner similar to FIG. 9. Before selecting one or more thumbnail images 85 in order to display their corresponding original images, the operator may select (or designate) one of the thumbnail images 85 with respect to each of the icons 84. In FIG. 13, the thumbnail images 85 marked with a circle are the selected ones. In response to the selection of each or all of the thumbnail images marked with a circle using the operation unit 6, an instruction input using the operation unit 6 after the selection, or an elapse of a predetermined time after the selection, the thumbnail images 85 are displayed in a manner that the thumbnail images 85 marked with a circle aligned with one another as shown in FIG. 14. This may be helpful for the operator to select thumbnail image(s) corresponding to desired image(s).

Figure 15:
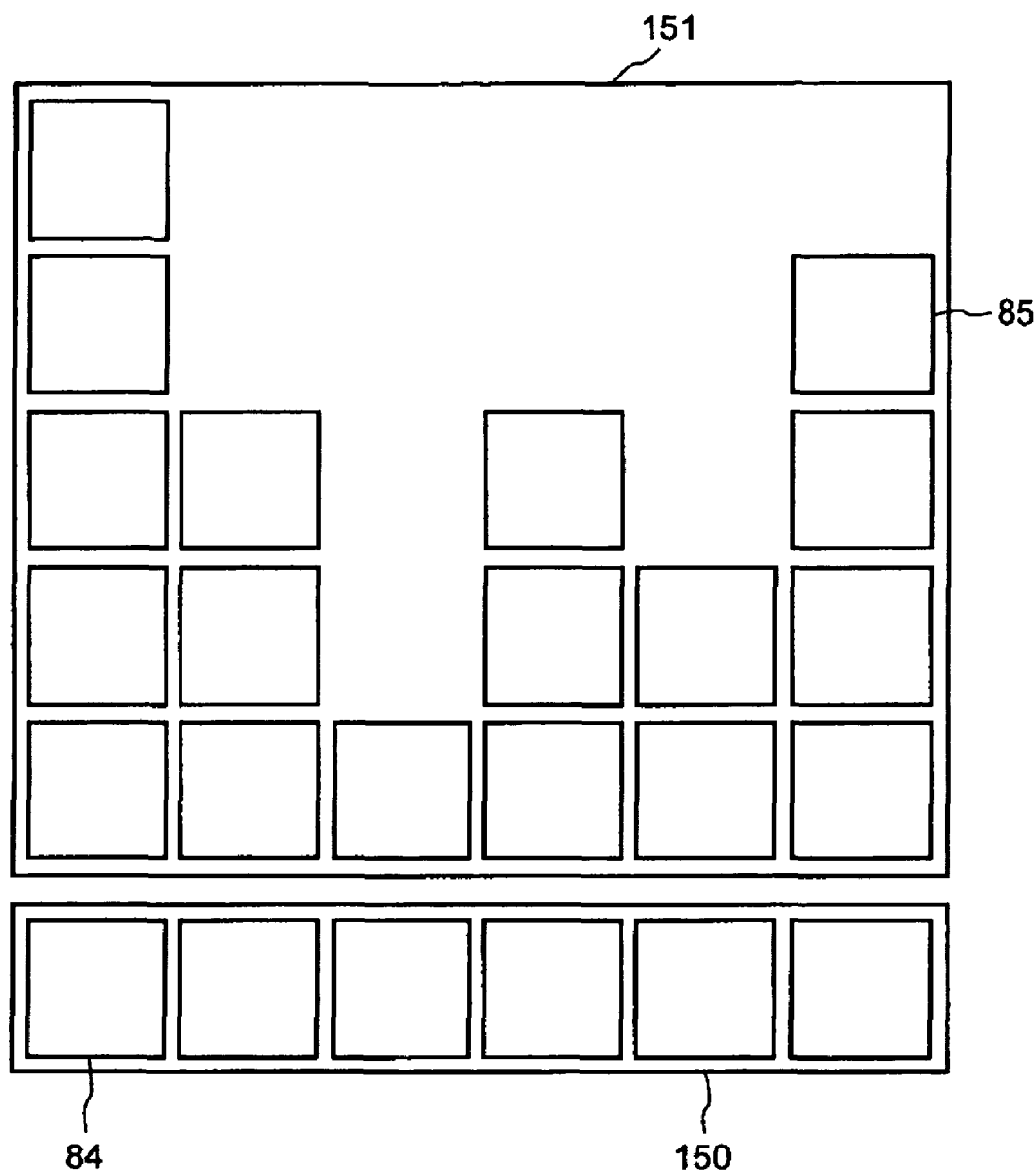
FIG. 15 is an illustration showing an example of the third modification to the display of thumbnail images according to the second embodiment.

FIG. 15 is an illustration showing an example of the third modification to the display of thumbnail images according to the second embodiment. As shown in FIG. 15, a touch panel 150 included in the operation unit 6 may be provided separately from the display unit 5 but operative as part of the display unit 5 so as to display the icons 84. Although FIG. 15 shows that the touch panel 150 is specially formed for displaying the icons 84, the touch panel 150 may be designed for inputting various types of information and the icons 84 may be only part of such information. The display unit 5 may display the thumbnail images 85 in a screen 151 with respect to the icons 84 displayed in the touch panel 150. The touch panel 150 may alternatively be provided on the screen 151 of the display unit 5. Further, a touch panel may also be provided for the thumbnail images 85 on the screen 151 of the display unit 5.

According to the second embodiment, the icons 84 representing the examination information and the thumbnail images 85 with respect to the icons 84 are displayed in parallel in the display unit 5, corresponding to each other. Therefore, the operator may not be required to change the display screens (or windows) back and forth in order to select examination information one after another, display thumbnail images, and see if there is a desired image. Further, the operator may be able to compare the thumbnail images with respect to different examinations without changing the display screen (or window). This may be helpful to make it easier for the operator to select thumbnail images corresponding to one or more desired images. Therefore, it may result in improving image observation (or diagnosis) efficiency.

In the embodiments described above, the icons have been prepared to represent examinations based on the examination information. Icons may, however, be prepared to represent sets of a series of images resulting from an X-ray computed tomography apparatus (hereinafter referred to as CT images). For example, the first icon may represent the first set of a series of CT images. The series of images included in the first set may be one hundred (100) slice images. In this case, the thumbnail images may be prepared based on the one hundred slice images included in the first set. Similarly, the second icon may represent the second set of a series of CT images. The series of images included in the second set may be fifty (50) slice images. In this case, the thumbnail images may be prepared based on the fifty slice images included in the second set.

The thumbnail images may alternatively be prepared, for example, every four-slice image of the one hundred slice images included in the first set. In this case, when the operator selects one of the thumbnail images, one original image corresponding to the selected thumbnail image and subsequent three original images may be displayed in parallel.

Figure 16:
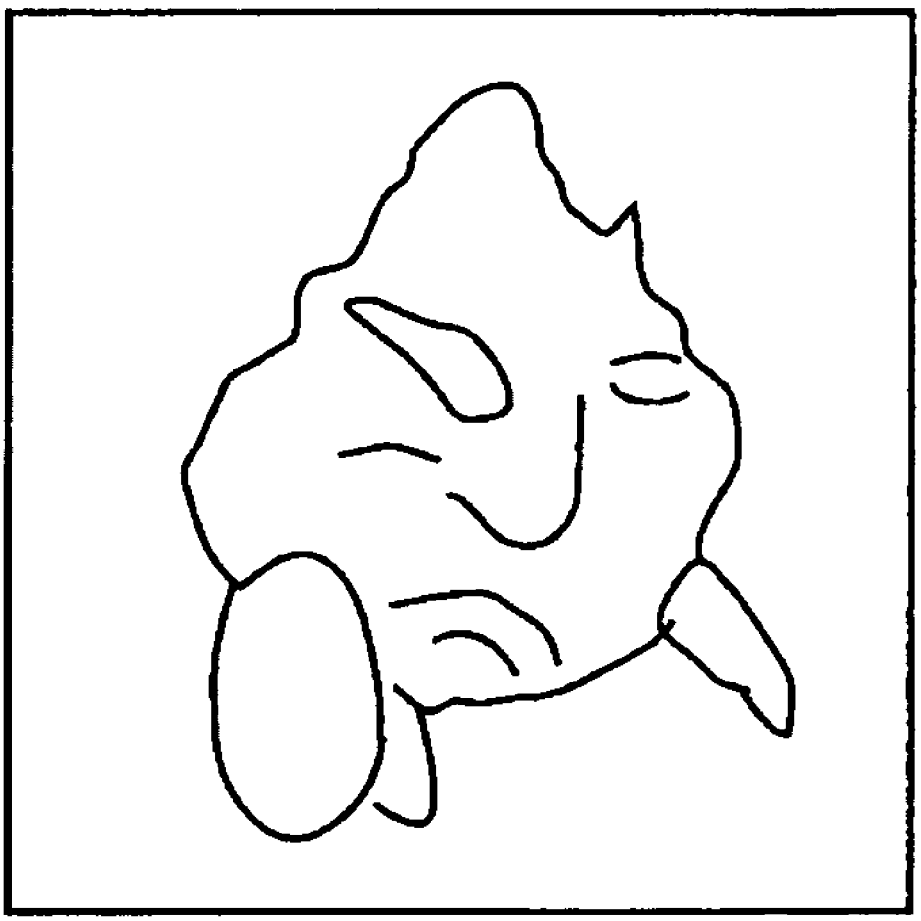
FIG. 16 is an illustration showing another example of the icon.

FIG. 16 is an illustration showing another example of the icon. When the icon represents a set of a series of CT images, the icon may be prepared to show a three-dimensional image prepared based on the series of CT images as shown in FIG. 16. Alternatively, one of the series of CT images may be shown in the icon. Further, the icon may show a predetermined or arbitrary cross-sectional surface of the three-dimensional image.

Icons and/or thumbnail images may also be prepared for ultrasound images resulting from an ultrasound diagnosis apparatus in a similar manner.

In the above embodiments, the icons may mean not only so-called icons but also any other possible pieces each of which showing information including at least information other than characters. As long as the information other than characters is shown in the piece, the piece may also show characters.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A medical image display apparatus, comprising:
a storage unit configured to hierarchically store a plurality of databases, each corresponding to a plurality of patient information stored in a first layer, a plurality of examination information corresponding to each of the plurality of patient information stored in a second layer, and a plurality of image data corresponding to each of the plurality of examination information corresponding to each of the plurality of patient information and stored in a third layer;
a processor configured to prepare a plurality of selectable icons, each icon based in the image data corresponding to one of the plurality of examination information corresponding to each of the plurality of patient information and stored in the second layer, and selectable thumbnail images associated with each of the plurality of selectable icons, each thumbnail image corresponding to an original medically scanned image;
a display unit configured to display, at a same time, the plurality of selectable icons based on selected patient information stored in the first layer and types of medically scanned image data corresponding to the plurality of examination information corresponding to the selected patient information and stored in the second layer, a first selectable icon showing a picture of a patient imaged for the image data, in an examination list displaying area positioned along one of a vertical direction or a horizontal direction in a screen, one icon corresponding to each of the plurality of examination information for the selected patient information, and to display the selectable thumbnail images associated with respective of the selectable icons in an image list displaying area positioned along the other one of the vertical direction or the horizontal direction, and an original image based on a selected thumbnail image, each of the selectable thumbnail images being displayed in a smaller size than the original image; and
an input unit configured to select one patient information of the plurality of patient information, a first of the plurality of selectable icons being selected by scrolling in the examination list displaying area and a first of the selectable thumbnail images being selected by scrolling in the image list displaying area, wherein the display unit is configured to display the original image corresponding to the selected thumbnail image, wherein the input unit is further configured to select a second of the plurality of selectable icons corresponding to a second of the plurality of examination information and a second of the selectable thumbnail images belonging to the second examination information, the display unit is further configured to switch to display the selectable thumbnail images belonging to the second examination information from the selectable thumbnail images belonging to a first examination, when the second selectable icon is selected by the input unit, and the display unit is still further configured to display in parallel the original image and a second original image, which corresponds to the second selectable thumbnail image, when the first and second selectable thumbnail images are selected by the input unit.

2. The apparatus according to claim 1, wherein the first selectable icon shows an imaged part of a patient in a first examination.

3. The apparatus according to claim 1, wherein the first selectable icon shows a type of an imaging apparatus generating the image data in a first examination.

4. The apparatus according to claim 1, wherein the first selectable icon includes a date of a first examination.

5. The apparatus according to claim 1, wherein the first selectable icon is displayed in a larger size than the first selectable thumbnail image of the selectable thumbnail images.

6. The apparatus according to claim 1, wherein the plurality of selectable icons are scrolled and displayed when all the plurality of selectable icons are not displayed in parallel in the display unit.

7. The apparatus according to claim 1, wherein the plurality of selectable icons are displayed in an order based on a predetermined priority condition.

8. The apparatus according to claim 1, wherein the plurality of selectable icons are displayed in an order as they were in a last use of the apparatus.

9. The apparatus according to claim 1, wherein the first selectable icon is selected through a touch panel included in the input unit.

10. The apparatus according to claim 1, wherein the first selectable thumbnail image of the selectable thumbnail images is selected through a touch panel included in the input unit.

11. The apparatus according to claim 1, wherein the selectable thumbnail images are scrolled and displayed when all the one or more selectable thumbnail images are not displayed in parallel in the display unit.

12. The apparatus according to claim 1, wherein the selectable thumbnail images are displayed in an order based on a predetermined priority condition.

13. The apparatus according to claim 1, wherein the selectable thumbnail images are displayed in an order as they were in a last use of the apparatus.

14. The apparatus according to claim 1, wherein,
the input unit is further configured to select a second and a third of the selectable thumbnail images, and
the display unit is further configured to display second and third original images in parallel corresponding to the second and the third selectable thumbnail images when the second and third selectable thumbnail images are selected by the input unit.

15. The apparatus according to claim 1, wherein the first selectable thumbnail image represents a plurality of images including the original image.

16. The apparatus according to claim 15, wherein the display unit is further configured to display the plurality of images when the first selectable thumbnail image is selected by the input unit.

17. A medical image display apparatus, comprising:
a storage unit configured to hierarchically store a plurality of databases, each corresponding to a plurality of patient information stored in a first layer, a plurality of examination information corresponding to each of the plurality of patient information stored in a second layer, and a plurality of image data corresponding to each of the plurality of examination information corresponding to each of the plurality of patient information and stored in a third layer;

a processor configured to prepare a plurality of selectable icons, each icon based in the image data corresponding to one of the plurality of examination information corresponding to each of the plurality of patient information stored in the second layer, and selectable thumbnail images associated with each of the plurality of selectable icons, each thumbnail image corresponding to an original medically scanned image;

a display unit configured to display, at a same time, the plurality of selectable icons based on selected patient information stored in the first layer and types of medically scanned image data corresponding to the plurality of examination information corresponding to the selected patient information and stored in the second layer, a first selectable icon showing a picture of a patient imaged for the image data, in an examination list displaying area positioned along one of a vertical direction or a horizontal direction in a screen, one icon corresponding to each of the plurality of examination information for the selected patient information, and to display the selectable thumbnail images associated with respective of the plurality of icons in an image list displaying area positioned along the other one of the vertical direction or the horizontal direction, and at least one original image based on a selected thumbnail image, each of the selectable thumbnail images being displayed in a smaller size than each of the at least one original image; and an input unit configured to select one patient information of the plurality of patient information and at least one of the selectable thumbnail images, which is selected by scrolling in the image list displaying area, wherein the display unit is configured to display at least one original image corresponding to the selected at least one of the selectable thumbnail images, wherein the input unit is further configured to select a second of the plurality of selectable icons corresponding to a second of the plurality of examination information and a second of the selectable thumbnail images belonging to the second examination information, the display unit is further configured to switch to display the selectable thumbnail images belonging to the second examination information from the selectable thumbnail images belonging to a first examination, when the second selectable icon is selected by the input unit, and the display unit is still further configured to display in parallel the original image and a second original image, which corresponds to the second selectable thumbnail image, when the first and second selectable thumbnail images are selected by the input unit.

18. The apparatus according to claim 17, wherein, when the display unit includes a first display screen and a second display screen, the plurality of selectable icons and the selectable thumbnail images are displayed in the first display screen and the at least one original image is displayed in the second display screen.

19. The apparatus according to claim 17, wherein, when a first of the selectable thumbnail images with respect to a first of the plurality of icons and a second of the selectable thumbnail images with respect to a second of the plurality of icons are selected by the input unit, the selectable thumbnail images with respect to the first icon and the one or more selectable thumbnail images with respect to the second icon are displayed in a manner that the first selectable thumbnail image is aligned with the second selectable thumbnail image.

20. A medical image display apparatus, comprising:
a storage unit configured to hierarchically store a plurality of databases, each corresponding to a plurality of patient information stored in a first layer, imaging information of a plurality of imaging operations stored in a second layer, and a plurality of image data sets resulting from the plurality of imaging operations corresponding to each of the plurality of patient information stored in a third layer, respectively, each of the image data sets including a series of images;
a processor configured to prepare a plurality of selectable icons, each icon based in the image data corresponding to one of the plurality of imaging operations corresponding to each of the plurality of patient information, and selectable thumbnail images associated with each of the plurality of selectable icons, each thumbnail image corresponding to an original medically scanned image;
a display unit configured to display, at a same time, the plurality of selectable icons based on selected patient information stored in the first layer and types of medically scanned image data sets corresponding to the plurality of imaging operations corresponding to the selected patient information, a first selectable icon showing a picture of a patient imaged for the image data sets, in an examination list displaying area positioned along one of a vertical direction or a horizontal direction in a screen, one icon corresponding to each of the plurality of imaging operations, and to display the selectable thumbnail images associated with respective of the selectable icons in an image list displaying area positioned along the other one of the vertical direction or the horizontal direction, and at least one of the series of images based on a selected thumbnail image, each of the selectable thumbnail images being displayed in a smaller size than each of the at least one of the series of images; and
an input unit configured to select one patient information of the plurality of patient information, one of the plurality of selectable icons, which is selected by scrolling in the examination list displaying area, and one of the selectable thumbnail images, which is selected by scrolling in the image list displaying area, so as to display one of the series of images associated with the selected icon and the selected thumbnail image, wherein
the display unit is configured to display the at least one of the series of images corresponding to the selected thumbnail image, wherein
the input unit is further configured to select a second of the plurality of selectable icons corresponding to a second of the plurality of examination information and a second of the selectable thumbnail images belonging to the second examination information,
the display unit is further configured to switch to display the selectable thumbnail images belonging to the second examination information from the selectable thumbnail images belonging to a first examination, when the second selectable icon is selected by the input unit, and
the display unit is still further configured to display in parallel the original image and a second original image, which corresponds to the second selectable thumbnail image, when the first and second selectable thumbnail images are selected by the input unit.

21. The apparatus according to claim 20, wherein the selected one of the selectable icons shows a three dimensional image based on the image data set resulting from a first imaging operation when the image data set results from an X-ray computed tomography apparatus.

22. The apparatus according to claim 20, wherein the selected one of the selectable icons shows a cross-sectional image obtained from a three dimensional image based on the image data set resulting from a first imaging operation when the image data set results from an X-ray computed tomography apparatus.

23. The apparatus according to claim 20, wherein the selected one of the selectable icons shows one of the series of images based on the image data set resulting from a first imaging operation.

24. A method of displaying a medical image, comprising:
hierarchically storing a plurality of databases, each corresponding to a plurality of patient information stored in a first layer, a plurality of examination information corresponding to each of the plurality of patient information stored in a second layer, and a plurality of image data corresponding to each of the plurality of examination information corresponding to each of the plurality of patient information and stored in a third layer;
preparing a plurality of selectable icons, each icon based in the image data corresponding to one of the plurality of examination information corresponding to each of the plurality of patient information stored in the second layer, and selectable thumbnail images associated with each of the plurality of selectable icons, each thumbnail image corresponding to an original medically scanned image;
displaying, at a same time, the plurality of selectable icons based on selected patient information stored in the first layer and types of medically scanned image data corresponding to the plurality of examination information corresponding to the selected patient information and stored in the second layer, a first selectable icon showing a picture of a patient imaged for the image data, in an examination list displaying area positioned along one of a vertical direction or a horizontal direction in a screen, one icon corresponding to each of the plurality of examination information for the selected patient information;
displaying selectable thumbnail images associated with respective of said plurality of selectable icons in an image list displaying area positioned along the other one of the vertical direction or the horizontal direction;
selecting one patient information of the plurality of patient information;
selecting a first of the plurality of selectable icons by scrolling in the examination list displaying area;
selecting a first of the selectable thumbnail images by scrolling in the image list displaying area; and
displaying an original image based on a selected thumbnail image, the original image being displayed in a larger size than the first selectable thumbnail image, the original image corresponding to the first selectable thumbnail image, wherein the displaying step includes displaying the original image corresponding to the selected thumbnail image, wherein the method further includes selecting a second of the plurality of selectable icons corresponding to a second of the plurality of examination information and a second of the selectable thumbnail images belonging to the second examination information, displaying the selectable thumbnail images belonging to the second examination information rather than the selectable thumbnail images belonging to a first examination, when the second selectable icon is selected, and displaying in parallel the original image and a second original image, which corresponds to the second selectable thumbnail image, when the first and second selectable thumbnail images are selected.

25. A method of displaying a medical image, comprising:

hierarchically storing a plurality of databases, each corresponding to a plurality of patient information stored in a first layer, a plurality of examination information corresponding to each of the plurality of patient information stored in a second layer, and a plurality of image data corresponding to the plurality of examination information corresponding to each of the plurality of patient information and stored in a third layer;

preparing a plurality of selectable icons, each icon based in the image data corresponding to one of the plurality of examination information corresponding to each of the plurality of patient information stored in the second layer, and selectable thumbnail images associated with each of the plurality of selectable icons, each thumbnail image corresponding to an original medically scanned image;

displaying the plurality of selectable icons based on selected patient information stored in the first layer and types of medically scanned image data corresponding to the plurality of examination information corresponding to the selected patient information and stored in the second layer, a first selectable icon showing a picture of a patient imaged for the image data, in an examination list displaying area positioned along one of a vertical direction or a horizontal direction in a screen, one icon corresponding to each of the plurality of examination information for the selected patient information;

displaying, at a same time as the plurality of selectable icons, selectable thumbnail images associated with respective of the plurality of icons in an image list displaying area positioned along the other one of the vertical direction or the horizontal direction;

selecting one patient information of the plurality of patient information and at least one of the selectable thumbnail images by scrolling in the image list displaying area; and displaying at least one original image based on a selected thumbnail image, the at least one original image being displayed in a larger size than each of the selectable thumbnail images, the at least one original image corresponding to the selected at least one of the selectable thumbnail images, wherein the method further includes selecting a second of the plurality of selectable icons corresponding to a second of the plurality of examination information and a second of the selectable thumbnail images belonging to the second examination information, displaying the selectable thumbnail images belonging to the second examination information rather than the selectable thumbnail images belonging to a first examination, when the second selectable icon is selected, and displaying in parallel the original image and a second original image, which corresponds to the second selectable thumbnail image, when the first and second selectable thumbnail images are selected.

26. A method of displaying a medical image, comprising:

hierarchically storing a plurality of databases, each corresponding to a plurality of patient information stored in a first layer, a plurality of examination information corresponding to each of the plurality of patient information stored in a second layer, and a plurality of image data corresponding to the plurality of examination information corresponding to each of the plurality of patient information and stored in a third layer;

preparing a plurality of selectable icons, each icon based in the image data corresponding to one of the plurality of examination information corresponding to each of the plurality of patient information stored in the second layer, and selectable thumbnail images associated with each of the plurality of selectable icons, each thumbnail image corresponding to an original medically scanned image;

displaying the plurality of selectable icons based on selected patient information stored in the first layer and types of medically scanned image data corresponding to the plurality of examination information corresponding to the selected patient information and stored in the second layer, a first selectable icon showing a picture of a patient imaged for the image data, in an examination list displaying area positioned along one of a vertical direction or a horizontal direction in a screen, one icon corresponding to each of the plurality of examination information for the selected patient information;

selecting one patient information of the plurality of patient information;

selecting a first of the plurality of selectable icons by scrolling in the examination list displaying area;

displaying, at a same time as the plurality of selectable icons, a first set of selectable thumbnail images in an examination list displaying area positioned along the other one of the vertical direction or the horizontal direction, the first set associated with a first of the plurality of examination information which corresponds to the first selectable icon;

selecting a second of the plurality of selectable icons by scrolling in the examination list displaying area;

switching display of the first set to a second set of selectable thumbnail images, the second set associated with a second of the plurality of examination information which corresponds to the second selectable icon;

selecting a first selectable thumbnail image from the second set; and displaying an original image corresponding to the first selectable thumbnail image based on the image data, the original image being displayed in a larger size than the first selectable thumbnail image, wherein the method further includes selecting a second of the plurality of selectable icons corresponding to a second of the plurality of examination information and a second of the selectable thumbnail images belonging to the second examination information, displaying the selectable thumbnail images belonging to the second examination information rather than the selectable thumbnail images belonging to a first examination, when the second selectable icon is selected, and displaying in parallel the original image and a second original image, which corresponds to the second selectable thumbnail image, when the first and second selectable thumbnail images are selected.

27. The medical image display apparatus according to claim 1, wherein the selectable thumbnail images belong to a first of the plurality of examination information associated with the first selectable icon, and the original image corresponds to the first selectable thumbnail image.

28. The medical image display apparatus according to claim 20, wherein, the selectable thumbnail images belong to a first of the plurality of imaging operations which corresponds to the selected one selectable icon, and the at least one of the series of images corresponds to the selected one selectable thumbnail image.

29. The method of claim 24, wherein said displaying selectable thumbnail images comprises:

displaying one or more selectable thumbnail images belonging to a first of the plurality of examination information which corresponds to the first selectable icon.

* * * * *